United States Patent [19]

Axén et al.

[11] Patent Number: 4,711,951

[45] Date of Patent: Dec. 8, 1987

[54] THERAPEUTICALLY ACTIVE COMPOUND AND PHARMACEUTICAL COMPOSITION CONTAINING THE SAME

[75] Inventors: Rolf E. A. V. Axén; Jan P. E. Carlsson, both of Uppsala, Sweden

[73] Assignee: Pharmacia Aktiebolag, Uppsala, Sweden

[21] Appl. No.: 594,981

[22] Filed: Mar. 29, 1984

Related U.S. Application Data

[63] Continuation of Ser. No. 364,675, Apr. 2, 1982, abandoned.

[30] Foreign Application Priority Data

Apr. 6, 1981 [SE] Sweden ................. 8102194

[51] Int. Cl.$^4$ ............................ C07K 5/02; C07K 7/02
[52] U.S. Cl. ............................................ 530/323
[58] Field of Search ................. 435/189, 190, 192; 260/112.7; 530/323

[56] References Cited

U.S. PATENT DOCUMENTS

| | | | |
|---|---|---|---|
| B471617 | 2/1976 | Kamber et al. | 260/112.7 |
| 3,481,917 | 12/1969 | Grant et al. | 260/112.7 |
| 4,144,128 | 3/1979 | Hildebrand et al. | 260/112.7 |
| 4,149,003 | 4/1979 | Carlsson | 546/261 |
| 4,220,722 | 9/1980 | Rowley et al. | 260/112.7 |
| 4,231,999 | 11/1980 | Carlsson | 424/1 |
| 4,232,119 | 11/1980 | Carlsson | 435/7 |
| 4,237,267 | 12/1980 | Okujama | 536/1 |
| 4,258,193 | 3/1981 | Fujii | 546/281 |
| 4,351,764 | 9/1982 | Birr | 260/112.7 |
| 4,430,266 | 2/1984 | Frank | 260/112.7 |
| 4,444,683 | 4/1984 | Kim et al. | 260/112.7 |

FOREIGN PATENT DOCUMENTS

| | | |
|---|---|---|
| 0017507 | 10/1980 | European Pat. Off. |
| 0023401 | 4/1981 | European Pat. Off. |
| 0030490 | 6/1981 | European Pat. Off. |
| 0031999 | 7/1981 | European Pat. Off. |
| 0023779 | 11/1981 | European Pat. Off. |
| 1416018 | 12/1975 | United Kingdom |
| 2034324 | 6/1980 | United Kingdom |
| 2040935 | 9/1980 | United Kingdom |

OTHER PUBLICATIONS

Biochemical Journal vol. 133 No. 1 May 1973 Molecular Aspects pp. 67–80 JP-A-55-22657 (Patent Abstr.).

*Primary Examiner*—Delbert R. Phillips
*Attorney, Agent, or Firm*—Fred Philpitt

[57] ABSTRACT

Therapeutically active organic compound exhibiting at least one radical comprising a structure —S'—S"—R, where S"—R is defined by R being an organic group comprised in a physiologically acceptable compound H—S"—R obtainable by the splitting of the disulfide bridge —S'—S"— in said structure, in which compound H—S"—R the sulfur atom S" is bound to a carbon atom in a heterocyclic aromatic ring in R having a configuration being such that the compound H—S"—R, while maintaining physiological acceptability, is stabilized, by tautomerism or resonance involving the sulfur atom S" bound to R, so as to be mainly excluded from further reaction involving thiol disulfide exchange; S' being bound to an aliphatic carbon atom; and said compound, in addition to the group or groups comprising the structure —S'—S"—R, also consisting of a residue of a therapeutically active organic base compound of polypeptide structure bound to S', for therapeutic use in mammals, including humans.

The invention also relates to a pharmaceutical composition containing as an active substance the compound mentioned above.

12 Claims, No Drawings

THERAPEUTICALLY ACTIVE COMPOUND AND PHARMACEUTICAL COMPOSITION CONTAINING THE SAME

This is a continuation of application Ser. No. 364,675, filed Apr. 2, 1982, now abandoned and the benefits of 35 USC 120 are claimed relative to it.

The present invention relates to a therapeutically active organic compound, which exhibits at least one radical comprising a structure —S'—S"—R, where S"—R is defined by R being an organic group comprised in a physiologically acceptable compound H—S"—R obtainable by the splitting of the disulfide bridge —S'—S"— in said structure, in which compound H—S"—R the sulfur atom S" is bound to a carbon atom in a heterocyclic aromatic ring in R having a configuration being such that the compound H—S"—R, while maintaining physiological acceptability, is stabilized, by tautomerism or resonance involving the sulfur atom S" bound to R, so as to be mainly excluded from further reaction involving thiol disulfide exchange; S' being bound to an aliphatic carbon atom; and said compound, in addition to the group or groups comprising the structure —S'—S"—R, also consisting of a residue of a therapeutically active organic base compound of polypeptide structure bound to S', for therapeutical use in mammals, including humans.

The invention also relates to a pharmaceutical composition containing said compound as an active substance.

(The different sulfur atoms have been labelled with ' and " for distinguishing of sulfur atoms directly bound to different molecular moieties.)

Polypeptides include proteins and are both examples of organic compounds exhibiting polypeptide structure. It is well known that proteins are polypeptides with a high molecular weight. Both proteins and polypeptides may have other structural parts as carbohydrate and lipid groups. Polypeptides thus also include glycoproteins and lipoproteins.

A number of organic compounds of polypeptide structure and of the type given above exhibiting at least one group comprising the structure —S'—S"—R have been described in e.g. "German Offenlegungschrift" No. 2 808 476. This publication deals with introducing pyridyldisulfide groups on antibodies and enzymes like alpha-amylase, alkaline phosphatase, catalase and peroxidase. These pyridyldisulfide derivatives were intermediates for conjugation of enzymes to antibodies labelling the latter. Thus these enzyme labelled antibodies were synthesized for use for immunoassays in vitro.

According to the present invention it has now been found that by derivatizing a therapeutically active organic compound of polypeptide structure containing (a) one or more carboxy groups and/or (b) one or more primary and/or secondary amino groups and/or (c) one or more SH—groups and/or inner —S—S— bridges to exhibit at least one structure —S'—S"—R, where S' and —S"—R is defined as above, certain advantageous and surprising effects can be accomplished in vivo.

Organic compounds of polypeptide structure, like enzymes and hormones, are usually excreted or otherwise eliminated relatively fast in mammals leading to a short duration for the activity these polypeptides. The activity of these types of substances may be essentially prolonged, when they are modified to derivatives according to the invention.

The explanation to this is probably that there are a large number of compounds comprising thiol groups in mammals, humans included. These thiol groups may react with therapeutically active polypeptides, which are derivatized according to the invention, in a thiol disulfide exchange reaction. Thus, the therapeutically active polypeptide will be bound in vivo.

Among organic compounds of polypeptide structure, which are interesting from a therapeutical point of view and being able to be modified to a compound according to the invention, therapeutical active proteins may be mentioned as for instance native enzymes as catalase, glutathione peroxidase and superoxide dismutase and hormones as insulin.

The compound according to the invention is used for treating diseases in mammals, humans included. The treatment includes the administration of a therapeutically effective amount of a compound according to the invention, preferably in form of a pharmaceutical composition.

The structures —S'—S"—R in the therapeutically active compound are always bound to a primary, secondary or tertiary aliphatic carbon atom, to which no other atoms except carbon and hydrogen are bound, i.e. the structure —S'—S"—R is preferably bound according to the formulas

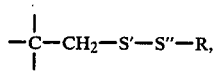

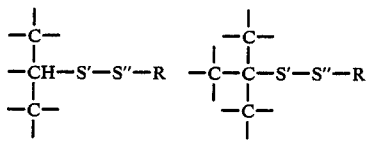

In general the structure —S'—S"—R is bound to an aliphatic carbon atom in a hydrocarbon chain, which may be straight, branched or cyclic and which also may be substituted. The structure —S'—S"—R may e.g. be bound to an aliphatic carbon atom in a group according to the formula —A—S'—S"—R, where A is a straight, branched or cyclic hydrocarbon chain of e.g. 1–10 carbon atoms. The chain may optionally be substituted with 1–3 hydroxyl groups and may optionally be broken by 1–3 oxygen or sulfur atoms, preferably at most one atom other than carbon and hydrogen being bound to one and the same carbon atom in the group A.

The therapeutically active compound can e.g. have at least one radical comprising a structure —S'—S"—R being substituted at a primary amino or secondary amino group or at a carboxy group in the therapeutically active organic base compound of polypeptide structure.

When the radical is substituted at a primary or secondary amino group, one or more of these amino groups of the base compound is preferably substituted by one group of the formula

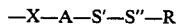  (I)

where A, R, S" and S' have the meanings given above and X is (1) the group —CO— bound to the nitrogen atom of the amino group or (2) a direct link to the nitrogen atom of the amino group.

When the radical is substituted at a carboxy group one or more carboxy groups —CO—OH in the base compound is preferably transformed to one or more groups of the formula

   (II)

where A, R, S'' have the meanings given above and $X^1$ is —O— or —N($R_1$)— where $R_1$ means hydrogen or a lower alkyl with 1–5 carbon atoms.

When the therapeutically active organic base compound of polypeptide structure contains one or more SH—groups and/or inner —S—S— bridges, at least one of these SH—groups or inner —S—S— bridges may have been transformed to said structure —S'—S''—R or to one or two such structures respectively.

According to the invention, the derivatization of the organic compound of polypeptide structure should not have profound negative effects on the therapeutical activity.

Direct binding of the alkyl residue A to the nitrogen atom of a primary or secondary amino group may be carried out e.g. by (a) substitution by use of a halogen compound (b) reduction of condensation products formed by reactions of amines with carbonyl groups for instance by hydrogenation and (c) Mannich condensation, i.e. a condensation at which a carbonyl compound together with a primary or secondary amine condense at a carbon atom having a reactive hydrogen. One particular carbonyl compound is formaldehyde.

There are many methods available for acylating a primary or secondary amino group in the base compound (i.e. for synthesis of derivatives in which X in formula (I) is —CO—). Usually compounds having reactive carboxy groups are used. Examples of such compounds are esters, e.g. p-nitro-phenyl esters, or anhydrides particularly unsymmetrical ones, e.g. unsymmetrical anhydrides formed by reaction between a carboxylic acid and the isobutyl ester of chloroformic acid, or compounds like acyl halides (—CO—Cl) and acyl azides (—CON$_3$). One particularly preferred activated structure is the O-acyl-isoureido structure, which is formed by reaction of carboxylic acids with carbodiimides particularly dicyclohexyl carbodiimide. Lactones are another type of a reactive carboxy compound. Thiollactones are particularly useful in connection with this invention, because simultaneous amidation and introduction of thiol groups are made possible. One well-known reagent is N-acetylhomocysteine-thiollactone.

These methods are also useful for transforming a carboxy group of the underivatized polypeptide to a group of formula (II), where $X^1$ is —N($R_1$)—.

There are many methods available for transforming a carboxy group to a group of formula (II), where $X^1$ is —O—. One particularly preferred method is esterification of alcohols promoted by dicyclohexyl carbodiimide as condensation agent and 4-dimethylaminopyridine as a suitable catalyst. This is a method offering mild reaction conditions. N,N'-carbonyldiimidazole is another example of a condensation agent also offering mild conditions. These condensation agents may be used for coupling of e.g. 3-(2-pyridinedithio)-propanol to polypeptides.

For direct substitution at a primary or secondary amino group by a substituent of formula (I), where X is a —CO— group bound to the nitrogen atom of the amino group, the amino group of the base compound may in principle be reacted in the same way as is described in "German Offenlegungschriften" Nos. 2 808 476 and 2 917 001. Accordingly said base compound may be reacted with a compound of formula R—S''—S'—A—Z (III), where R has the same meanings as given above, preferably, 2-pyridyl, 5-nitro-2-pyridyl, 4-pyridyl, 5-carboxy-2-pyridyl, the N-oxide of any of these four groups, especially 2-pyridyl-N-oxide, or 2-benzothiazolyl, A, S' and S'' have the same meanings as given before and Z is a group.

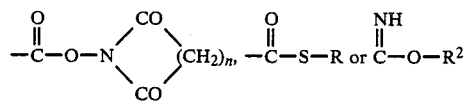

or acid addition salts thereof, where n is 2 or 3, R is identical with and of the same meanings as given above and $R^2$ is methyl or ethyl. Preferably A is —CH$_2$—CH$_2$— and Z is

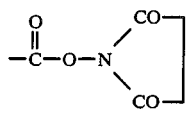

The preparation of compounds according to formula (III), where R is 2-pyridyl, 5-nitro-2-pyridyl, 4-pyridyl and 5-carboxy-2-pyridyl, has been described in U.S. Pat. No. 4,149,003. The preparation of the corresponding N-oxides and of compounds of formula (III), with R being 2-benzothiazolyl is carried out analogously (compare "German Offenlegungschrift" No. 2 917 001).

The reaction of the therapeutically active organic compound containing amino groups with a compound of formula (III) may be carried out in aqueous solutions of pH 5–8 containing 1–10 percent (v/v) of a water-miscible organic solvent, which organic solvent does not give negative effects on the therapeutically active compound. Examples of such solvents are ethanol and methanol usually used at a temperature of 20°–25° C. The reaction between an amino group containing therapeutically active compound (T—NH$_2$) and N-succinimidyl-3-(2-pyridyldithio)-propionate is represented as follows:

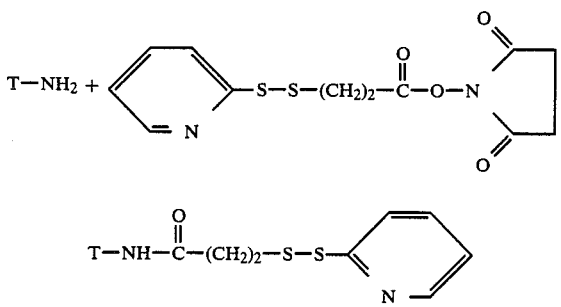

The structure —S'—S''—R may also be introduced in two steps. The first step is introduction of a thiol group, e.g. with a known thiolating agent. One such agent is a thiolimidate of the formula

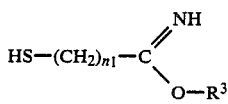

where $R^3$ is methyl or ethyl and $n_1$ is an integer 1–10, preferably 2–4. One other thiolating agent is N-acetyl-homocysteine thiol lactone. The second step is reaction of the thiol compound formed with a symmetric disulfide of formula

where R has the same meanings as above.

The first step is carried out in aqueous solution in slightly alkaline milieu (pH 7–9) and at 15°–30° C. The thiolating agent is used in a large excess.

The second step is carried out in aqueous solutions at pH 2–9 and at a temperature of 15°–30° C. The disulfide is used in a large excess. A water-miscible organic solvent, e.g. ethanol, may be added to speed up the dissolution of the disulfide. The organic solvent does not give negative effects on the therapeutically active derivative.

When the therapeutically active organic base compound already contains one or more SH-groups, the structure —S'—S"—R may be directly introduced by reaction with a compound of formula (V) above and at the conditions mentioned above.

Base compounds containing inner —S—S— bridges may be reacted with an excess of a low molecular thiol compound for splitting of said bridges to form SH-groups. Usually dithiothreitol is used as splitting agent preferably at pH 6–9. The excess of reduction agent is removed by dialysis or gel filtration preferably at a weak acidic pH and in absence of oxygen. The thiol groups formed are in a second step reacted at a pH of 2–9 and with a large excess of disulfide of formula (V) as described above. If necessary the solubility of the disulfide (V) may be increased by adding a water-miscible organic solvent, e.g. ethanol, which does not have a negative effect on the polypeptide.

The invention also relates to a pharmaceutical composition being characterized in containing as active substance at least one therapeutically active compound, which is derivatized according to the invention.

The compound may according to the invention be used in the same administration forms which are regular for the therapeutically active base compound. The compound is, however, preferably used in the form of solutions or suspensions for injection or infusion.

The dosage varies with the choice of compound and the desired therapeutic effect. As indicated above, the dosage of a number of compounds may, according to the invention, be increased (estimated on molar basis) compared to the dosage of the base compounds due to increased tolerance for the new compounds. In other cases the dosage may be lower than the dosage of base compound still with obtaining the corresponding therapeutic effect due to a lower decomposition rate.

The invention will now be illustrated with some examples.

EXAMPLE 1

Insulin-2-pyridyl disulfide derivative

Synthesis 20 mg insulin was dissolved in 2 ml 0.1M sodium phosphate buffer of pH 7.4 and containing 5% ethanol (v/v). 15 mg N-succinimidyl-3-(2-pyridyldithio)-propionate (SPDP from Pharmacia Fine Chemicals AB, Uppsala, Sweden) was added and the reaction mixture wa stirred for 90 minutes at +25° C. Thereafter 2 ml of said phosphate buffer (without ethanol) was added and the solution was gel filtrated on a column packed with particles of epichlorohydrin cross-linked dextran (Sephadex ®G-25, Pharmacia Fine Chemicals AB). The particles had been equilibrated in an aqueous solution of 0.9% NaCl (w/v) before gel filtration. Elution was carried out with 0.9% NaCl (w/v). The void fractions containing insulin-2-pyridyl disulfide derivative were pooled and kept at +4° C.

Examination of pharmacological qualities

Test animals were white mice (male mice of type NMRI) having a body weight of 25±2 g. The solutions below were administrated intravenously in the tails of the mice. There were three groups of mice, in which there were three mice each. The solutions contained:

Group A: 0.5 ml 0.9% (w/v) NaCl

Group B: 0.5 ml 0.9% (w/v) NaCl and 5 ug native insulin

Group C: 0.5 ml 0.9% (w/v) NaCl 50 ug insulin-2-pyridyl disulfide derivative synthesized as above.

Blood samples were collected in micro capillary tubes from the corners of the eyes of the mice. The samples were collected 10 minutes before injection and 30, 120, 240 minutes, 7, 15 and 24 hours on injection. The anthrone method was used to determine the carbohydrate content of the samples (Burt J R; Anal Biochem, 9 (1964) p 293–302).

Injection of 0.9% (w/v) NaCl (group A) gave no significant change in the blood sugar level and for all time intervals it was equivalent to 2 mg glucose/ml serum. On injection of 5 ug native insulin (group B) and 50 ug insulin-2-pyridyl disulfide derivative (group C) the blood sugar level was reduced to 40% of the normal value in 30 minutes. The blood sugar level of the mice of group B reached the normal value (value before injection) in 7 hours. The blood sugar level of the mice of group C did not return to normal values until after 24 hours, i.e. the insulin-2-pyridyl disulfide derivative has a longer duration in comparison to native insulin, which may be explained in terms of a longer half-life for the derivative.

EXAMPLE 2

Superoxide dismutase-2-pyridyl disulfide derivative

Synthesis 30 mg superoxide dismutase (from yeast, Carlsbergs Laboratories, Copenhagen, Denmark) was dissolved in 0.88 ml 0.1M sodium phosphate buffer, pH 7.5. 0.12 ml SPDP (24 mM in ethanol (99.5% v/v)) was added and the reaction mixture was vigorously shaken and left for 30 minutes at +25° C. The solution was thereafter gel filtrated on a column packed with Sepadex ®G-25 equilibrated with 0.9% (w/v) NaCl. The column was then eluted with 0.9% (w/v) NaCl and the void fractions containing the superoxide dismutase-2-pyridyl disulfide derivative were collected, pooled and kept at +4° C.

Determination of half-life for circulation in rabbit

Test animals were white rabbits having a body weight of 2-5 kg. 1 ml native superoxide dismutase (yeast superoxide dismutase, Carlsberg Laboratories, Copenhagen, Denmark) (10 mg/ml) or 1 ml superoxide dismutase-2-pyridyl disulfide derivative (10 mg/ml) was injected intravenously into the rabbits. Both of the solutions were prepared from 0.9% (w/v) NaCl. Blood samples were collected from the ear lobes of the rabbits at the time intervals 5, 10, 20, 30, 60, 90, 120, 150, 180 and 210 minutes. The superoxide dismutase activity of the samples was determined according to Crapo J D, McCord J M and Fridovich I; Methods of Enzymology 53 (1978) p 382-393.

The half-life for native superoxide dismutase was found to be about 10 minutes, while the corresponding value for the superoxide dismutase-2-pyridyl disulfide derivative was 60 minutes. Thus, a prolonged time for circulation of superoxide dismutase-2-pyridyl disulfide derivative was found.

EXAMPLE 3

Catalase-2-pyridyl disulfide derivative

Synthesis

Catalase of bovine liver (Sigma C-100 from Sigma Chemical Company, St. Louis, Mo, USA) was further purified by gel filtration on agarose (Sepharose ®CL 6B from Pharmacia Fine Chemicals AB, Uppsala, Sweden). 13 mg purified catalase in 1.5 ml 0.1M sodium phosphate buffer pH 8 was mixed with 0.15 ml SPDP (32 mM in 99.5% (v/v) ethanol). The reaction mixture was vigorously shaken and kept for 60 minutes at +25° C. The solution was thereafter gel filtrated on a column packed with Sephadex ®G-25 equilibrated with 0.9% (w/v) NaCl. The column was eluted with 0.9% (w/v) NaCl and the void fractions containing catalase-2-pyridyl disulfide derivative were collected and kept at +4° C.

Examination of pharmacological qualities

Test animals were white rats (Sprague Dawley) of a body weight of 300-350 g. Two groups of rats (6 individuals each) were separately injected intravenously with 0.5 ml 0.9% (w/v) NaCl containing 20,000 international units (IU) native catalase respectively an amount of catalase-2-dipyridyl disulfide derivative (synthesized as above) corresponding to 20,000 (IU) native catalase. 5 minutes after injection hind paws of all the rats were burnt by dipping into circulating water of +55° C. for 20 seconds. 0.4 ml blood was collected from the left arteriae carotis at the time intervals 2, 15, 30, 60, 120 and 180 minutes. The catalase activity in each blood sample was determined as the amount of oxygen formed per time unit. Measurements were carried out with a Clark electrode by standard procedures.

Under these conditions the half-lifes for circulating native catalase and its 2-pyridyl disulfide derivative were found to be 9 minutes and 34 minutes respectively. The circulation time for catalase-2-pyridyl disulfide was thus significantly prolonged.

The oedema of the burn was measured as the volume of the paw. This volume was measured as corresponding displacement at even time cuts during 3 hours. In 2 hours there was a significantly decreased swelling of the paws of those rats to which catalase-2-pyridyl disulfide had been administered compared to the paws of those to which native catalase had been administered.

We claim:

1. The method for prolonging the activity of organic base compounds of polypeptide structure having known therapeutic activity, which known compounds contain
   (a) one or more carboxy groups, and/or
   (b) one or more primary and/or secondary amino groups, and/or
   (c) one or more SH-groups and/or inner —S—S— bridges such method of prolonging the activity comprising substituting a group comprising the structure —S'—S"—R for the groups (a) or (b) or transforming one of the groups of (c) into the structure —S'—S"—R, wherein R is selected from the group consisting of
   (1) 2-benzothiazolyl,
   (2) 5-nitro-2-pyridyl
   (3) 2-pyridyl
   (4) 4-pyridyl
   (5) 5-carboxy-2-pyridyl and
   (6) the N-oxides of any of (2) to (5)
   and S' is bound to an aliphatic carbon atom, such substitution or transformation having no profound negative effects on therapeutical activity.

2. A method according to claim 1 wherein said base compound is a therapeutically active enzyme or hormone.

3. The method according to claim 1 wherein said base compound of polypeptide structure having known therapeutic activity is selected from the group consisting of catalase, glutathione peroxidase, superoxide dismutase and insulin.

4. A method according to claim 1 wherein one or more of said amino groups of (b) is substituted with a group of the formula —X—A—S'—S"—R, wherein R and S' have the meanings set forth in claim 1, A is a straight, branched or cyclic hydrocarbon chain of 1-10 carbon atoms which is unsubstituted or substituted with 1-3 hydroxyl groups and is non-broken or broken by 1-3 oxygen or sulfur atoms, at most one atom other than carbon and hydrogen being bound to one and the same carbon atom in A, and X is (1) the function —CO— bound to the nitrogen atom of the amino group or (2) a direct bond to the nitrogen atom of the amino group.

5. A method according to claim 1 wherein one or more of the carboxyl groups of (a) is transformed to a group of the formula —CO—$X^1$—A—S'—R—S"—R, wherein A, R and S' have the meanings set forth in claim 3 and $X^1$ is —O— or —N($R_1$)—, wherein $R_1$ is a hydrogen atom or a lower alkyl group of 1-5 carbon atoms.

6. A method according to claim 1 wherein said base compound is insulin and R is 2-pyridyl.

7. A method according to claim 1 wherein said base compound is superoxide dismutase and R is 2-pyridyl.

8. A method according to claim 1 wherein said base compound is catalase and R is 2-pyridyl.

9. A method according to claim 2 wherein one or more of said amino groups of (b) is substituted with a group of the formula —X—A—S'—S"—R, wherein R and S' have the meanings set forth in claim 1, A is a straight, branched or cyclic hydrocarbon chain of 1-10 carbon atoms which is unsubstituted or substituted with 1-3 hydroxyl groups and is non-broken or broken by 1-3 oxygen or sulfur atoms, at most one atom other than carbon and hydrogen being bound to one and the same carbon atom in A, and X is (1) the function —CO— bound to the nitrogen atom of the amino group or (2) a direct bond to the nitrogen atom of the amino group.

10. A method according to claim 2 wherein one or more of the carboxyl groups of (a) is transformed to a group of the formula —CO—$X^1$—A—S'—R—S"—R, wherein A, R and S' have the meanings set forth in claim 3 and $X^1$ is —O— or —N($R_1$)—, wherein $R_1$ is a hydrogen atom or a lower alkyl group of 1-5 carbon atoms.

11. A method according to claim 3 wherein one or more of said amino groups of (b) is substituted with a group of the formula —X—S—S'—S"—R, wherein R and S' have the meanings set forth in claim 1, A is a straight, branched or cyclic hydrocarbon chain of 1-10 carbon atoms which is unsubstituted or substituted with 1-3 hydroxyl groups and is non-broken or broken by 1-3 oxygen or sulfur atoms, at most one atom other than carbon and hydrogen being bound to one and the same carbon atom in A, and X is (1) the function —CO— bound to the nitrogen atom of the amino group or (2) a direct bond to the nitrogen atom of the amino group.

12. A method according to claim 3 wherein one or more of the carboxyl groups of (a) is transformed to a group of the formula —CO—$X^1$—A—S'—R'S"—R, wherein A, R and S' have the meanings set forth in claim 3 and $X^1$ is —O— or —N($R_1$)—, wherein $R_1$ is a hydrogen atom or a lower alkyl group of 1-5 carbon atoms.

* * * * *